United States Patent [19]

Augustine et al.

[11] Patent Number: 5,189,006

[45] Date of Patent: Feb. 23, 1993

[54] PALLADIUM-TIN CATALYSTS FOR ACYLOXYLATION OF ALKYLAROMATIC COMPOUNDS

[75] Inventors: Robert L. Augustine, Livingston; Setrak K. Tanielyan, South Orange, both of N.J.

[73] Assignees: Philip Morris Incorporated, New York, N.Y.; Philip Morris Products Inc., Richmond, Va.

[21] Appl. No.: 842,646

[22] Filed: Feb. 27, 1992

Related U.S. Application Data

[62] Division of Ser. No. 788,447, Nov. 6, 1991.

[51] Int. Cl.$^5$ .............................................. B01J 23/62
[52] U.S. Cl. .................................................... 502/339
[58] Field of Search ....................... 502/242, 339, 333

[56] References Cited

U.S. PATENT DOCUMENTS 4,830,844 5/1989 Kolts ................................. 502/339 X

OTHER PUBLICATIONS

Bryant et al., *Journal of Organic Chemistry*, 34 (No. 4) pp. 1106–1108 (1969).

*Primary Examiner*—W. J. Shine
*Attorney, Agent, or Firm*—James E. Schardt

[57] ABSTRACT

This invention provides process embodiments for acyloxylation of $C_1$–$C_4$ alkylaromatic compounds to produce alpha-acyloxy $C_1$–$C_4$ alkyl-substituted aromatic compounds, utilizing a palladium-tin catalyst which exhibits efficient oxidation selectivity and oxidation rate stability.

Toluene is acetoxylated to benzyl acetate and benzylidene diacetate.

3 Claims, 1 Drawing Sheet

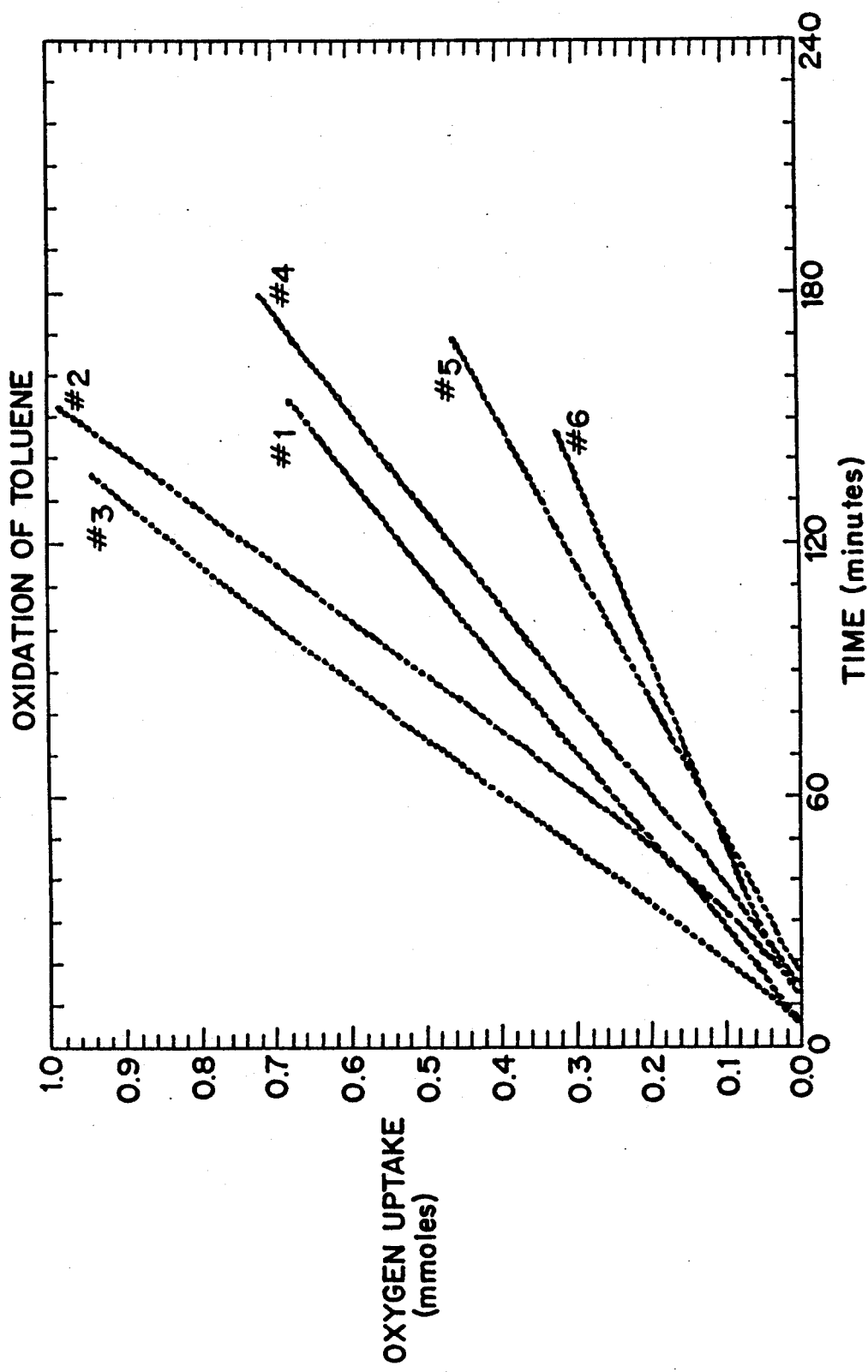

PALLADIUM-TIN CATALYSTS FOR ACYLOXYLATION OF ALKYLAROMATIC COMPOUNDS

This application is a division of application Ser. No. 07/788,447, filed Nov. 6, 1991.

BACKGROUND OF THE INVENTION

New methods have been reported in the scientific literature for the direct conversion of alkylaromatic compounds to esters.

Journal of Organic Chemistry, 34 (No. 4), 106 (1969) describes a palladium-catalyzed conversion of xylene to xylyl acetate, p-xylylene diacetate and p-methylbenzylidene diacetate. The xylene oxidation is conducted in acetic acid, employing a palladium-stannous acetate catalyst and air.

Oxidation Communications, 7 (Nos. 1-2), 69 (1984) describes the kinetics of toluene oxidation to benzyl acetate in the presence of $Pd(OAc)_2$, $Sn(OAc)_2$ and KOAc. The active catalytic species is a heterogeneous combination of palladium, tin and oxygen.

Of related interest with respect to the present invention are U.S. Pat. Nos. 4,317,460; 4,524,051; and 4,855,274. These references disclose palladium-tin and other catalysts for the oxidation of carbon monoxide to carbon dioxide.

There is continuing interest in the development of stable catalyst systems for oxidation of organic compounds with high selectivity and efficiency.

Accordingly, it is an object of this invention to provide an improved palladium-tin catalyst for selective oxidation of organic compounds.

It is a further object of this invention to provide a process for acyloxylation of a $C_1$-$C_4$ alkyl-substituted aromatic compound to an alpha-acylox $C_1$-$C_4$ alkyl-substituted aromatic compound, with a palladium-tin catalyst exhibiting high oxidation efficiency and a stable oxidation rate.

Other objects and advantages of the present invention shall become apparent from the accompanying description and examples.

DESCRIPTION OF THE INVENTION

One or more objects of the present invention are obtained by the provision of a process for preparing a palladium-tin oxidation catalyst which comprises (1) treating a suspension of particulate inorganic support substrate in an aqueous medium with a tin salt under basic conditions to form a coating of tin hydroxide on the support surface; (2) treating the tin-coated support substrate suspension in an aqueous medium with a water-soluble palladium salt to form a palladium-tin metal complex coating on the support substrate surface; and (3) recovering and drying the metal complex-coated support substrate to provide a catalyst for selective oxidation of organic compounds.

In a preferred embodiment as demonstrated in Example II, this invention provides a process for preparing a palladium-tin oxidation catalyst which comprises (1) treating a suspension of particulate inorganic support substrate in an aqueous medium with a basic reagent to activate the support substrate surface; (2) treating the aqueous medium suspension of support substrate with a tin salt under basic conditions to form a coating of tin hydroxide on the activated support substrate surface; (3) treating the tin-coated support substrate suspension in an aqueous medium with a water-soluble palladium salt to form a palladium-tin metal complex coating on the support substrate surface; and (4) recovering and drying the metal complex-coated support substrate to provide a catalyst for selective oxidation of organic compounds.

The sequential immobilization of the multiple metal ions on the surface of the support substrate as described above imparts improved catalytic properties as compared to catalysts prepared by simultaneous incipient-wetness absorption of the metal salts on the support substrate. A preferred present invention catalyst exhibits efficient selective oxidation activity and oxidation rate stability under organic compound acyloxylation conditions. The immobilized metal species on the support substrate are not leached into the reaction medium during a liquid phase type of oxidation reaction.

The support substrate for the catalysts is selected from conventional porous and nonporous materials which include silica, alumina, titania, magnesia, natural and synthetic zeolites, and the like. The support material typically has an average particle size in the range between about 10-200 microns, and the support materials with porous structures have a pore size between about 3-500 angstroms.

The tin salt employed for catalyst preparation is selected from $Sn^{+2}$ and $Sn^{+4}$ chlorides, nitrates, sulfates, carboxylates, and the like. A preferred type of tin salt is a tin(II) chloride having the formula $SnCl_2 \cdot 2H_2O$. The tin content of a catalyst varies in the range between about 0.1-20 weight percent, and usually is in the range between about 2-5 weight percent, based on the catalyst weight.

The palladium metal component of the catalyst can be added in the form of a water-soluble chloride, nitrate, sulfate, carboxylate, or the like, such as palladium chloride or sodium tetrachloropalladate of the formula $Pd(Cl)_2$ or $Na_2PdCl_4$. The ratio of tin to palladium (Sn:Pd) in the catalyst coating layer is in the range between about 1:1 and 5:1.

Optionally, the palladium salt component can be in admixture with another salt of a noble metal such as ruthenium, rhodium, rhenium, osmium, iridium, platinum or gold. The ratio of palladium to noble metal preferably will vary in the range between about 10:0.1 to 10:2.

A suitable basic reagent for use in catalyst preparation includes alkali metal and ammonium hydroxide, carbonate or bicarbonate, as exemplified by sodium hydroxide, potassium hydroxide, lithium hydroxide, and ammonium carbonate. The pH of the catalyst slurry medium after precipitation of the tin hydroxide on the support substrate surface is in the range of about 2-8.

A water medium is utilized during the catalyst preparation, or an aqueous medium mixture of water and a water-miscible organic solvent such as tetrahydrofuran or dimethylformamide.

The catalyst preparation steps can be conducted at ambient temperature. The rate and uniformity of palladium ion deposition on the tin hydroxide-coated support substrate particles is improved if the catalyst slurry is maintained at a temperature between about 30°-60° C. during the palladium salt addition step.

The catalyst solids can be separated from the slurry medium by filtration or centrifugation. The recovered catalyst preferably is washed with water to remove any chloride ion that is present, and provide a catalyst which is chlorine-free.

Prior to use the prepared catalyst usually is dried by heating at a temperature of 100°–500° C. in an inert atmosphere such as helium. The drying procedure also can be accomplished by heating the catalyst under reduced pressure.

In another embodiment this invention provides a selective oxidation process which comprises reacting a $C_1$–$C_4$ alkylaromatic compound with oxygen in the presence of carboxylic acid and a palladium-tin catalyst to produce an alpha-acyloxy $C_1$–$C_4$ alkyl-substituted aromatic compound; wherein the catalyst is a product of a preparative process which comprises (1) treating a suspension of particulate inorganic support substrate in an aqueous medium with a tin salt under basic conditions to form a coating of tin hydroxide on the support surface; (2) treating the tin-coated support substrate suspension in an aqueous medium with a water-soluble palladium salt to form a palladium-tin metal complex coating on the support substrate surface; and (3) recovering and drying the metal complex-coated support substrate to provide a catalyst for selective oxidation of organic compounds.

In a further embodiment this invention provides a selective oxidation process which comprises reacting a $C_1$–$C_4$ alkylaromatic compound with oxygen in the presence of carboxylic acid and a palladium-tin catalyst to produce an alpha-acyloxy $C_1$–$C_4$ alkyl-substituted aromatic compound; wherein the catalyst is a product of a preparative process which comprises (1) treating a suspension of particulate inorganic support substrate in an aqueous medium with a basic reagent to activate the support substrate surface; (2) treating the aqueous medium suspension of support substrate with a tin salt under basic conditions to form a coating of tin hydroxide on the activated support substrate surface; (3) treating the tin-coated support substrate suspension in an aqueous medium with a water-soluble palladium salt to form a palladium-tin metal complex coating on the support substrate surface; and (4) recovering and drying the metal complex-coated support substrate to provide a catalyst for selective oxidation of organic compounds.

The oxidation process can be conducted either under liquid phase or gas phase conditions, and can be operated as a continuous reaction system.

Illustrative of $C_1$–$C_4$ alkylaromatic compounds which can be acyloxylated in accordance with the present invention are toluene, xylene, mesitylene, n-butylbenzene, isopropylbenzene, 1-methylnaphthalene, 4-ethylpyridine, 2-methylfuran, and the like.

The carboxylic acid component of the oxidation reaction system in general can be a compound corresponding to the formula:

$$R-CO_2H$$

where R is a $C_1$–$C_{12}$ organic substituent which is stable under the oxidation conditions. Suitable carboxylic acids include acetic acid, 2-fluoroacetic acid, butanoic acid, cyclohexanecarboxylic acid, benzoic acid, 4-methoxybenzoic acid, 4-pyridinecarboxylic acid, 2-naphthalenecarboxylic acid, and the like. The carboxylic acid component usually is provided in a molar excess relative to the $C_1$–$C_4$ alkylaromatic compound.

The oxygen reactant can be provided as pure oxygen, or as a component of a gasiform mixture such as air. The oxidation reaction can be conducted at subatmospheric, atmospheric or superatmospheric pressure, at a temperature between about 20°–150° C. for a reaction period between about 0.5–20 hours sufficient to complete the selective oxidative conversion of the $C_1$–$C_4$ alkylaromatic starting material.

If one of the $C_1$–$C_4$ alkylaromatic or carboxylic acid reactants is a solid at the oxidation reaction temperature, a solvent medium such as benzene or tetrahydrofuran can be incorporated in the reaction system.

The acetoxylation of toluene proceeds with the following stoichiometry:

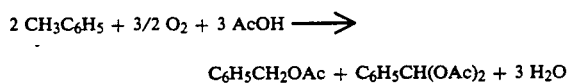

$$2\ CH_3C_6H_5 + 3/2\ O_2 + 3\ AcOH \longrightarrow$$

$$C_6H_5CH_2OAc + C_6H_5CH(OAc)_2 + 3\ H_2O$$

The mechanism of the oxidative catalysis is believed to involve a palladium-tin redox system:

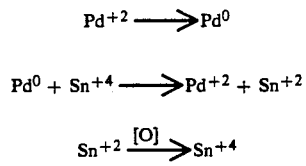

$$Pd^{+2} \longrightarrow Pd^{0}$$

$$Pd^{0} + Sn^{+4} \longrightarrow Pd^{+2} + Sn^{+2}$$

$$Sn^{+2} \xrightarrow{[O]} Sn^{+4}$$

Palladium with a plus two valence appears to be the active catalytic metal species in the acyloxylation reaction.

BRIEF DESCRIPTION OF THE DRAWING

With reference to the specification drawing, FIG. 1 is a graphic representation of the oxygen gas utilization rates for the oxidative acetoxylation of toluene over different palladium-tin catalysts as described in Example III and summarized in Table I.

The following examples are further illustrative of the present invention. The components and specific ingredients are presented as being typical, and various modifications can be derived in view of the foregoing disclosure within the scope of the invention.

EXAMPLE I

This Example illustrates the preparation of palladium-tin catalysts in accordance with the present invention.

A 250 ml three-necked flask equipped with a magnetic stirring bar, thermometer, bubbler and a septum was charged with 15 ml of $H_2O$ and 5 g of $SiO_2$ (Davidson grade 952, acid washed, calcined at 400° C. for 4 hours, 80–120 mesh, BET surface area of 332.5 $m^2/g$). To this suspension was added with stirring 16.8 ml of a $SnCl_2.2\ H_2O$ solution (1.28 g of $SnCl_2.2\ H_2O$ and 0.4 ml of 6 M HCl in 100 ml of $H_2O$) at a rate of 10 ml/min., and the mixture was stirred for 30 minutes. To the resulting suspension was added 18.8 ml of sodium hydroxide (2.4 g of NaOH in 500 ml of water) at a rate of 10–15 ml/min. The aqueous medium of the slurry had a pH value of 4–4.2 and gave a negative test for $Sn^{+2}$ (characteristic reaction with $HAuCl_3$).

The reaction vessel was purged with He for 10 minutes at a flow rate of 20 ml/min., and immersed in a silicon oil bath heated at 55° C. When the temperature of the slurry reached 45°–50° C., 8.4 ml of a $Na_2PdCl_4$ solution (1.66 g of $Na_2PdCl_4$ dissolved in 100 ml of water) was added at a rate of 2–3 ml/min., and the mixture was stirred for 30 minutes. The slurry solids were separated by centrifugation and washed several times with a dilute acetic acid solution (pH, 4-4.2) until the absence of a detectable quantity of Cl− in the washing liquid (AgNO₃). The resulting catalyst product (1% wt of Pd) was dried in air at 95° C. for 12 hours. The catalyst then was loaded in a Pyrex glass tube (0.30/0.006 m/m) in two portions with a He flow of 20 ml/min. and with a temperature program of 10 min. at 25° C., ramping at 20°/min. to 300° C., and holding at 300° C. for two hours.

In a similar manner, rhodium-palladium-tin catalysts are prepared by including rhodium nitrate with the palladium salt during the sequential addition steps.

EXAMPLE II

This Example illustrates a modified process for the preparation of a palladium-tin catalyst which exhibits selective oxidation activity and improved oxidation rate stability under toluene acetoxylation conditions.

The procedures of Example I were followed, except that the support substrate was activated by pretreatment with a basic reagent.

A 250 ml three-necked flask equipped with a magnetic stirring bar, thermometer, bubbler and a septum was charged with 15 ml of H₂O and 5 g of SiO₂ (Davidson grade 952, acid washed, calcined at 400° C. for 4 hours, 80-120 mesh, BET surface area of 332.5 m²/g). To this suspension was added with stirring 9.4 ml of sodium hydroxide (2.4 g of NaOH in 500 ml of water) at the rate of 10-15 ml/min. The mixture was stirred for 15 minutes, and 16.8 ml of a SnCl₂ 2 H₂O solution (1.28 g of SnCl₂ 2 H₂O and 0.4 ml of 6 M HCl in 100 ml of H₂O) was added at a rate of 10 ml/min., and the mixture was stirred for 30 minutes. To the resulting suspension was added a second portion of 9.4 ml of sodium hydroxide at a rate of 10-15 ml/min. The aqueous medium of the slurry had a pH value of 4-4.2 and gave a negative test for Sn²⁺.

The reaction vessel was purged with He for 10 minutes at a flow rate of 20 ml/min. The temperature of the slurry mixture was increased to 50° C., and 8.4 ml of a Na₂PdCl₄ solution (1.66 g of Na₂PdCl₄ dissolved in 100 ml of water) was added at a rate of 2-3 ml/min., and the mixture was stirred for 30 minutes. The slurry solids were separated by centrifugation and washed several times with a dilute acetic acid solution (pH, 4-4.2) until the absence of a detectable quantity of Cl− in the washing liquid (AgNO₃). The resulting catalyst product (1% wt of Pd) was dried in air at 95° C. for 12 hours. The catalyst then was loaded in a Pyrex glass tube (0.30/0.006 m/m) in two portions with a He flow of 20 ml/min. and with a temperature program of 10 min. at 25° C., ramping at 20° C./min. to 300° C., and holding at 300° C. for two hours.

EXAMPLE III

This Example illustrates the preparation of palladium-tin catalysts, and the use of the catalysts for the selective acetoxylation of toluene.

Using the same procedures described in Example I, catalysts were prepared having a range of different concentrations of SnCl₂ and Na₂PdCl₄ (with the same atomic ratio of Sn:Pd=2). The relative activities of samples #1-6 in Table I and FIG. 1 were measured in connection with the selective oxidation of toluene. The rate of oxygen consumption was measured as a criterion of catalyst activity. During each toluene oxidation run, the accumulation of benzyl acetate(l) and benzylidene diacetate(2) was monitored using GC analysis, and in all the cases the ratio of (1):(2) was in the range of 3-3.2:1.

For each toluene oxidation run, 1 gram of a supported Pd-Sn catalyst, 0.392 gram of KOAc (0.4 mol/1), 1.4 ml of toluene (1.3 mol/1) and 8.6 ml of acetic acid were charged to a reactor. The system was alternately evacuated and filled with oxygen three times. The pressure was adjusted to atmospheric, and the reaction flask was placed in thermostating bath set at 70° C. After a two minute equilibration time, the uptake of supplied oxygen (about 0.25 cc pulse volume) was measured using a computerized monitoring system. After the rate of oxygen uptake decreased significantly as indicating a near complete reaction, an aliquot of reaction medium was withdrawn from the reactor and analyzed by gas chromatography. The product mixture was composed of benzyl, acetate and benzylidene diacetate in near quantitative yield.

TABLE I

| # | % Pd | Rate, mmol O₂/min. |
|---|------|---------------------|
| 1 | 0.75 | 4.80 × 10³ |
| 2 | 1.00 | 7.83 |
| 3 | 1.25 | 7.60 |
| 4 | 1.50 | 4.47 |
| 5 | 1.90 | 3.02 |
| 6 | 2.60 | 2.51 |

EXAMPLE IV

This Example illustrates the selective acetoxylation of xylene in accordance with the present invention.

The same procedures and stoichiometry of Example III were followed, except that a xylene isomer mixture was substituted for the toluene reactant. The oxidation reaction was conducted for a period of 20 hours, and the resultant product mixture had the composition summarized in Table II.

TABLE II

| Xylene | % conversion | %⁽¹⁾ cpd. 1 | % cpd 2 | % cpd 3 | % cpd 4 |
|--------|--------------|-------------|---------|---------|---------|
| ortho  | 59.2 | 34.1 | 2.5 | 19.2 | 3.4 |
| meta   | 48.6 | 26.5 | 3.8 | 13.0 | 5.3 |
| para   | 40   | 21.8 | 1.4 | 10.4 | 6.4 |

⁽¹⁾Cpd 1 methylbenzyl acetate
Cpd 2 methylbenzylidine diacetate
Cpd 3 acetoxymethylbenzyl acetate
Cpd 4 acetoxymethylbenzylidene diacetate

What is claimed is:

1. A process for preparing a palladium-tin oxidation catalyst which comprises (1) treating a suspension of particulate inorganic support substrate in an aqueous medium with a basic reagent to activate the support substrate surface; (2) treating the aqueous medium suspension of support substrate with a tin salt under basic conditions to form a coating of tin hydroxide on the activated support substrate surface; (3) treating the tin-coated support substrate suspension in an aqueous medium with a water-soluble palladium salt to form a palladium-tin metal complex coating on the support substrate surface; and (4) recovering and drying the metal complex-coated support substrate to provide a catalyst for selective oxidation of organic compounds.

2. A process in accordance with claim 1 wherein the treatment in step(3) is with a palladium salt and at least one other water-soluble noble metal salt to form a polymetallic complex coating on the support substrate surface.

3. A palladium-tin oxidation catalyst produced in accordance with the process of claim 1.

* * * * *